(12) United States Patent
Shea

(10) Patent No.: US 8,057,360 B2
(45) Date of Patent: Nov. 15, 2011

(54) EXERCISE SYSTEM

(76) Inventor: Michael J. Shea, Vienna, VA (US)

( * ) Notice: Subject to any disclaimer, the term of this patent is extended or adjusted under 35 U.S.C. 154(b) by 0 days.

(21) Appl. No.: 12/890,635

(22) Filed: Sep. 25, 2010

(65) Prior Publication Data

US 2011/0015041 A1    Jan. 20, 2011

Related U.S. Application Data

(60) Continuation of application No. 10/150,012, filed on May 20, 2002, now Pat. No. 7,824,310, which is a continuation of application No. 09/541,986, filed on Apr. 3, 2000, now abandoned, which is a continuation of application No. 09/317,980, filed on May 25, 1999, now abandoned, which is a continuation of application No. 08/869,166, filed on Jun. 4, 1997, now abandoned, which is a division of application No. 08/493,541, filed on Jun. 22, 1995, now abandoned.

(51) Int. Cl.
*A63B 71/00* (2006.01)
(52) U.S. Cl. ............ 482/8; 482/1; 482/9; 482/901
(58) Field of Classification Search ............. 482/1–9, 482/900–902
See application file for complete search history.

(56) References Cited

U.S. PATENT DOCUMENTS

| | | |
|---|---|---|
| 3,767,195 A | 10/1973 | Dimick |
| 4,112,928 A | 9/1978 | Putsch |
| 4,278,095 A | 7/1981 | Lapeyre |
| 4,358,105 A | 11/1982 | Sweeney, Jr. |
| 4,408,613 A | 10/1983 | Relyea |
| 4,542,897 A | 9/1985 | Melton et al. |
| 4,544,152 A | 10/1985 | Taitel |
| 4,549,044 A | 10/1985 | Durham |
| 4,556,216 A | 12/1985 | Pitkanen |
| 4,566,461 A | 1/1986 | Lubell et al. |
| 4,571,682 A | 2/1986 | Silverman et al. |
| 4,642,769 A | 2/1987 | Petrofsky |
| 4,702,475 A | 10/1987 | Elstein et al. |
| 4,708,337 A | 11/1987 | Shyu |
| 4,709,917 A | 12/1987 | Yang |
| 4,720,789 A | 1/1988 | Hector et al. |
| 4,729,560 A | 3/1988 | Cho |
| 4,740,912 A | 4/1988 | Whitaker |
| 4,763,284 A | 8/1988 | Carlin |
| 4,786,049 A | 11/1988 | Lautenschlager |
| 4,828,257 A * | 5/1989 | Dyer et al. ............ 482/5 |

(Continued)

FOREIGN PATENT DOCUMENTS

DE       41 00 559       7/1991

(Continued)

OTHER PUBLICATIONS

Universal® Physical Conditioning Equipment, 1985 Catalog, pp. 9-11.

(Continued)

*Primary Examiner* — Glenn Richman

(57) ABSTRACT

An example system includes a processor and communication circuitry under the control of the processor. The communication circuitry is configured to communicate exercise programs to exercise apparatuses, the communicated exercise programs including a first exercise program for use in controlling an exercise apparatus of a first exercise type and a second exercise program for use in controlling an exercise apparatus of a second exercise type different than the first exercise type.

23 Claims, 9 Drawing Sheets

U.S. PATENT DOCUMENTS

| | | | |
|---|---|---|---|
| 4,831,242 A | 5/1989 | Englehardt et al. | |
| 4,840,372 A | 6/1989 | Oglesby et al. | |
| 4,842,266 A | 6/1989 | Sweeney, Sr. et al. | |
| 4,842,274 A | 6/1989 | Oosthuizen et al. | |
| 4,860,763 A | 8/1989 | Schminke | |
| 4,907,795 A | 3/1990 | Shaw et al. | |
| 4,919,418 A * | 4/1990 | Miller | 482/6 |
| 4,934,694 A * | 6/1990 | McIntosh | 482/9 |
| 4,998,725 A | 3/1991 | Watterson et al. | |
| 5,006,983 A | 4/1991 | Wayne et al. | |
| 5,020,795 A | 6/1991 | Airy et al. | |
| 5,054,774 A | 10/1991 | Belsito | |
| 5,062,632 A | 11/1991 | Dalebout et al. | |
| 5,067,710 A | 11/1991 | Watterson et al. | |
| 5,076,584 A | 12/1991 | Openiano | |
| 5,076,587 A | 12/1991 | Manley | |
| 5,089,960 A | 2/1992 | Sweeney, Jr. | |
| 5,104,120 A | 4/1992 | Watterson et al. | |
| 5,137,501 A | 8/1992 | Mertesdorf | |
| 5,142,358 A | 8/1992 | Jason | |
| 5,149,084 A | 9/1992 | Dalebout et al. | |
| 5,180,347 A | 1/1993 | Chen | |
| 5,207,621 A | 5/1993 | Koch et al. | |
| 5,213,555 A | 5/1993 | Hood et al. | |
| 5,230,673 A | 7/1993 | Maeyama et al. | |
| 5,240,417 A | 8/1993 | Smithson et al. | |
| 5,243,998 A | 9/1993 | Silverman et al. | |
| 5,246,411 A | 9/1993 | Rackman | |
| 5,256,115 A | 10/1993 | Scholder et al. | |
| 5,277,678 A | 1/1994 | Friedebach et al. | |
| 5,308,296 A | 5/1994 | Eckstein | |
| 5,308,300 A | 5/1994 | Chino et al. | |
| 5,314,391 A | 5/1994 | Potash et al. | |
| 5,318,491 A | 6/1994 | Houston | |
| 5,335,188 A | 8/1994 | Brisson | |
| 5,354,251 A | 10/1994 | Sleamaker | |
| 5,361,091 A | 11/1994 | Hoarty et al. | |
| 5,368,546 A | 11/1994 | Stark et al. | |
| 5,374,227 A | 12/1994 | Webb | |
| 5,383,826 A | 1/1995 | Michael | |
| 5,385,519 A | 1/1995 | Hsu et al. | |
| 5,387,164 A | 2/1995 | Brown, Jr. | |
| 5,403,252 A | 4/1995 | Leon et al. | |
| 5,407,402 A | 4/1995 | Brown et al. | |
| 5,410,471 A | 4/1995 | Alyfuku et al. | |
| 5,410,472 A | 4/1995 | Anderson | |
| 5,429,361 A | 7/1995 | Raven et al. | |
| 5,435,799 A | 7/1995 | Lundin | |
| 5,462,503 A | 10/1995 | Benjamin | |
| 5,462,504 A | 10/1995 | Trulaske et al. | |
| 5,466,200 A | 11/1995 | Ulrich et al. | |
| 5,474,090 A | 12/1995 | Begun et al. | |
| 5,489,249 A | 2/1996 | Brewer et al. | |
| 5,493,692 A | 2/1996 | Theimer et al. | |
| 5,502,806 A | 3/1996 | Mahoney et al. | |
| 5,512,025 A | 4/1996 | Dalebout et al. | |
| 5,516,334 A | 5/1996 | Easton | |
| 5,527,239 A | 6/1996 | Abbondanza | |
| 5,547,439 A | 8/1996 | Rawls et al. | |
| 5,553,860 A | 9/1996 | Zelikovich | |
| 5,577,981 A | 11/1996 | Jarvik | |
| 5,584,779 A | 12/1996 | Knecht et al. | |
| 5,591,104 A | 1/1997 | Andrus et al. | |
| 5,598,849 A | 2/1997 | Browne | |
| 5,643,094 A | 7/1997 | Macri et al. | |
| 5,645,509 A | 7/1997 | Brewer et al. | |
| 5,645,513 A | 7/1997 | Haydocy et al. | |
| 5,647,747 A | 7/1997 | Macri et al. | |
| 5,655,997 A | 8/1997 | Greenberg et al. | |
| 5,667,459 A | 9/1997 | Su | |
| 5,690,582 A | 11/1997 | Ulrich et al. | |
| 5,702,323 A | 12/1997 | Poulton | |
| 5,704,875 A | 1/1998 | Tanabe | |
| 5,706,822 A | 1/1998 | Khavari | |
| 5,711,671 A | 1/1998 | Geeslin et al. | |
| 5,720,619 A | 2/1998 | Fisslinger | |
| 5,734,886 A | 3/1998 | Grosse et al. | |
| 5,749,372 A | 5/1998 | Allen et al. | |
| 5,777,895 A | 7/1998 | Kuroda et al. | |
| 5,779,596 A | 7/1998 | Weber | |
| 5,785,630 A | 7/1998 | Bobick et al. | |
| 5,785,631 A | 7/1998 | Heidecke | |
| 5,785,632 A | 7/1998 | Greenberg et al. | |
| 5,787,175 A | 7/1998 | Carter | |
| 5,810,747 A | 9/1998 | Brudny et al. | |
| 5,836,770 A | 11/1998 | Powers | |
| 5,845,230 A | 12/1998 | Lamberson | |
| 5,862,325 A | 1/1999 | Reed et al. | |
| 5,888,172 A | 3/1999 | Andrus et al. | |
| 5,890,906 A | 4/1999 | Macri et al. | |
| 5,890,995 A | 4/1999 | Bobick et al. | |
| 5,890,997 A | 4/1999 | Roth | |
| 5,905,442 A | 5/1999 | Mosebrook et al. | |
| 5,916,063 A | 6/1999 | Allesandri | |
| 5,929,782 A | 7/1999 | Stark | |
| 5,931,763 A | 8/1999 | Allesandri | |
| 5,944,633 A | 8/1999 | Wittrock | |
| 5,947,869 A | 9/1999 | Shea | |
| 5,949,951 A | 9/1999 | Sklar et al. | |
| 5,961,332 A | 10/1999 | Joao | |
| 5,978,770 A | 11/1999 | Waytena et al. | |
| 5,997,476 A | 12/1999 | Brown | |
| 6,004,243 A | 12/1999 | Ewert | |
| 6,033,344 A | 3/2000 | Trulaske et al. | |
| 6,042,519 A | 3/2000 | Shea | |
| 6,044,205 A | 3/2000 | Reed et al. | |
| 6,050,924 A | 4/2000 | Shea | |
| 6,056,670 A | 5/2000 | Shu et al. | |
| 6,059,692 A | 5/2000 | Hickman | |
| 6,066,075 A | 5/2000 | Poulton | |
| 6,152,856 A | 11/2000 | Studor et al. | |
| 6,167,401 A | 12/2000 | Csipkes et al. | |
| 6,171,218 B1 | 1/2001 | Shea | |
| 6,193,631 B1 | 2/2001 | Hickman | |
| 6,336,891 B1 | 1/2002 | Fedrigon et al. | |
| 6,450,922 B1 | 9/2002 | Henderson et al. | |
| 6,464,618 B1 | 10/2002 | Shea | |
| 6,497,638 B1 | 12/2002 | Shea | |
| 6,615,241 B1 | 9/2003 | Miller et al. | |
| 6,638,198 B1 | 10/2003 | Shea | |
| 6,659,916 B1 | 12/2003 | Shea | |
| 6,749,537 B1 | 6/2004 | Hickman | |
| 6,808,472 B1 | 10/2004 | Hickman | |
| 7,056,265 B1 | 6/2006 | Shea | |
| 7,510,509 B2 | 3/2009 | Hickman | |
| 7,575,536 B1 | 8/2009 | Hickman | |
| 7,621,846 B2 | 11/2009 | Ainsworth | |
| 7,625,315 B2 | 12/2009 | Hickman | |
| 7,637,847 B1 | 12/2009 | Hickman | |
| 7,678,023 B1 | 3/2010 | Shea | |
| 7,824,310 B1 | 11/2010 | Shea | |
| 2004/0162189 A1 | 8/2004 | Hickman | |
| 2005/0233861 A1 | 10/2005 | Hickman | |
| 2006/0281603 A1 | 12/2006 | Hickman | |

FOREIGN PATENT DOCUMENTS

| | | |
|---|---|---|
| EP | 0 199 442 | 10/1986 |
| JP | 2003-132186 | 5/2003 |
| WO | 94/17860 | 8/1994 |
| WO | 96/22134 | 7/1996 |
| WO | 96/38205 | 12/1996 |
| WO | 97/18534 | 5/1997 |
| WO | 98/00204 | 1/1998 |
| WO | 98/32496 | 7/1998 |

OTHER PUBLICATIONS

Miley, Michael, "Groupware Technology Moves to the Internet", MacWeek, vol. 10, n1, p. 73(2), Jan. 1997.
Application No. 375,616 filed Jan. 1995.
Shea, U.S. Appl. No. 13/225,470, filed Sep. 4, 2011.
Shea, U.S. Appl. No. 13/175,904, filed Jul. 4, 2011.
Shea, U.S. Appl. No. 12/890,632, filed Sep. 25, 2010.
Shea, U.S. Appl. No. 12/780,916, filed May 16, 2010.
Shea, U.S. Appl. No. 12/778,067, filed May 11, 2010.
Shea, U.S. Appl. No. 12/363,748, filed Jan. 31, 2009.
Shea, U.S. Appl. No. 10/728,880, filed Dec. 8, 2003.

Brown, S., "Video Cycle Race", Popular Science, 1989 (1 page).

Manning, R., "Videogame Players Get a Workout with the Exertainment", The Courier-Journal, Sep. 25, 1994.

"The New Exertainment System", Life Fitness, 1995 (1 page).

"The Race Begins with $85", Randal Sports, 1990 (1 page).

Skorupa, J., "Virtual Fitness", Popular Mechanics, Oct. 1994 (3 pages).

Netpulse, Ad Resource: Internet Advertising and Promotion Resources, http://web.archive.org/web/20000820192238/http://adres.internet.com/advertising/networks/print/0,1401,8371 215771,00.html, printable version, Oct. 11, 1999, 1 page.

Netpulse, Ad Resource: Internet Advertising and Promotion Resources, http://web.archive.org/web/20000816090822/http://adres.internet.com/advertising/networks/article/0,1401,8371 215771,00.html, screen shot, Oct. 11, 1999, 2 pages.

Netpulse Frequent Fitness Program Instructions, http://www.netpulse.com/html/members/programs/frequentfitness.html, 1998, 2 pages.

"24 Hour Fitness Partners with Netpulse", Netpulse—Press Releases, http://web.archive.org/web/20010119102700/www.netpulse.net/press/releases/19980309.html, Mar. 9, 1998, 2 pages.

"Netpulse Makes Working Out More Than a Calorie-Burning Session", Netpulse—Press: Releases, http://web.archive.org/web/20010119105500/www.netpulse.net.press/releases/19980302.html, Mar. 2, 1998, 2 pages.

Ad Resource: Search Results, 1 page.

\* cited by examiner

| 1 | PROGRAM | NAME AND DESCR. |
| 2 | PROGRAM | NAME AND DESCR. |
| 3 | PROGRAM | NAME AND DESCR. |
| ... | ... | ... |
| n | PROGRAM | NAME AND DESCR. |

FIG. 8

EXERCISE SYSTEM

CROSS-REFERENCE TO RELATED APPLICATIONS

This application is a continuation of application Ser. No. 10/150,012, filed May 20, 2002, which is a continuation of application Ser. No. 09/541,986, filed Apr. 3, 2000, which is a continuation of application Ser. No. 09/317,980, filed May 25, 1999, which is a continuation of application Ser. No. 08/869,166, filed Jun. 4, 1997, which is a divisional of application Ser. No. 08/493,541, filed Jun. 22, 1995, the entire contents of each of which is hereby incorporated by reference in this application.

BACKGROUND

1. Technical Field

The present invention generally relates to an exercise apparatus and, more particularly, to an exercise apparatus which transmits data to and receives data from a remote location.

2. Description of Related Art

Many exercisers currently utilize one or more exercise devices in their training routines. These exercise devices include, for example, weight machines, stair climbers, rowing machines, treadmills, and stationary bicycles. Some of these devices are controllable by microcomputers in accordance with exerciser-selected programs which set and/or vary the exercise level during program execution. FIGS. 1 and 2 illustrate a stationary bicycle 5 which provides automatically-varying exercise levels as disclosed in U.S. Pat. No. 4,358,105 to Sweeney, Jr. The control system for the stationary bicycle includes a microcomputer 10 which communicates electronically with a keyboard 12, a read-only memory 14, and a display 16. The read-only memory 14 stores the operating program for microcomputer 10 and a plurality of pre-stored exercise programs which are selectable by an exerciser. Movement of pedals 20 rotates a sprocket 22, which causes a chain 24 to drive a small diameter sprocket 26 attached to a flywheel 28. The variable load which an exerciser must overcome in order to rotate sprocket 22 is generated by an alternator 30, which provides a variable resistance to the effort of the exerciser through its driving connection with flywheel 28 by a gear belt 32. Microcomputer 10 controls the loading circuit of alternator 30. The output of microcomputer 10 on line 34 is a pulse width modulated signal, the width of which is proportional to the effort required by the exerciser. The changes in pulse width vary the field current in the alternator to cause variations in the resistance of the alternator to the force exerted by the operator. An exerciser using the stationary bicycle may select a pre-stored exercise program from read-only memory 14 for execution by microcomputer 10 to automatically vary the exercise difficulty level by generating pulses whose width is a function of the effort required by the exerciser. Using keyboard 12, an exerciser is also able to select a difficulty level and an exercise time.

From workout to workout, an exerciser will often select different exercise programs and set different difficulty levels and/or exercise times in order, for example, to achieve particular fitness goals and/or to avoid injury. Thus, for example, an exerciser may select an exercise program, difficulty level, and exercise time which define a relatively easy workout on a day following a hard workout. In addition, after several months of a training routine, an exerciser will likely find that he or she is able to use an exercise device at higher difficulty levels and/or for longer exercise times. Thus, an exerciser will likely find that he or she is capable of pedaling a stationary bicycle in accordance with selected exercise programs for a longer exercise time at a higher difficulty level than at the beginning of the training routine. Similarly, an exerciser using a weight machine will likely find that he or she will be able to perform more repetitions using more weight (or resistance) after several months of a training program.

However, the memories of exercise apparatus of the type described above are typically programmed by the manufacturer and cannot be changed by dealers or consumers. Thus, such exercise apparatus generally provide only a limited number of exercise programs from which an exerciser may select. While a manufacturer could provide a greater number of pre-stored exercise programs, this would require an increase in the size of read-only memory 14, thereby increasing costs. And even if a larger memory were provided for storing more programs, the memory contents would still not be changeable by dealers and/or consumers and the manufacturer would still not be ensured that the exercise programs satisfy the requirements of all exercisers, particularly exercisers having specific exercise needs or goals. The fixed memory contents may also lead to boredom on the part of the exerciser who must repeatedly choose an exercise program from the same selection of exercise programs. This boredom may cause the exerciser to reduce, or even stop, using the exercise apparatus.

SUMMARY

In accordance with one aspect of the present invention, an exercise apparatus includes an exercise device, a memory including a first memory portion, and a receiver for receiving exercise programs transmitted over a first communication link. A control unit supplies received exercise programs to the first memory portion for storage in the first memory portion as first exercise programs and selectively controls the exercise device in accordance with the first exercise programs.

In accordance with another aspect of the present invention, a method of operating an exercise apparatus including an exercise device and a memory with a first memory portion includes the steps of receiving exercise programs transmitted over a first communication link, supplying received exercise programs to the first memory portion for storage in the first memory portion as first exercise programs, and selectively controlling the exercise device in accordance with the first exercise programs.

In accordance with another aspect of the present invention, a central office for an exercise system includes generating circuitry for generating an exercise program for controlling an exercise device and a transmitter for transmitting the exercise program over a communication link.

In accordance with yet another aspect of the present invention, a method of providing exercise programs for controlling an exercise device includes the steps of generating an exercise program for controlling an exercise device and transmitting the exercise program over a communication link.

In accordance with yet another aspect of the present invention, an exercise system includes a central office having generating circuitry for generating an exercise program for controlling an exercise device and a transmitter for transmitting the exercise program over a communication link. The exercise system further includes at least one exercise apparatus including an exercise device, a memory including a first memory portion, and a receiver for receiving exercise programs transmitted over the communication link. The exercise apparatus further includes a control unit for supplying the received exercise programs to the first memory portion for storage in the first memory portion as first exercise programs and for selectively controlling the exercise device in accordance with the first exercise programs.

In accordance with another aspect of the present invention, a method of operating an exercise device including a memory having a first memory portion includes the steps of generating an exercise program for controlling an exercise device, transmitting the exercise program over a communication link, receiving exercise programs transmitted over the communication link, supplying received exercise programs to the first memory portion for storage in the first memory portion as first exercise programs, and selectively controlling the exercise device in accordance with the first exercise programs.

Thus, in accordance with the present invention, the memory of an exercise apparatus may be downloaded with exercise programs from a remote location. As new exercise programs are developed for exercise apparatus, these programs may be easily supplied to apparatus already "in the field." In addition, exercise apparatus may be provided with the capability of uploading data to a central office to permit monitoring of the use of an exercise apparatus and of the selection of exercise programs. The present invention provides the further ability to transmitting text data including messages, news headlines, sports scores, stock market prices, weather reports, advertisements, and the like for display at the exercise apparatus to provide a mental activity during exercise.

BRIEF DESCRIPTION OF THE DRAWINGS

FIG. 8 is a table depicting an organization of exercise programs stored on portable memory module 103.

DETAILED DESCRIPTION OF EXAMPLE EMBODIMENTS

Figure 3:
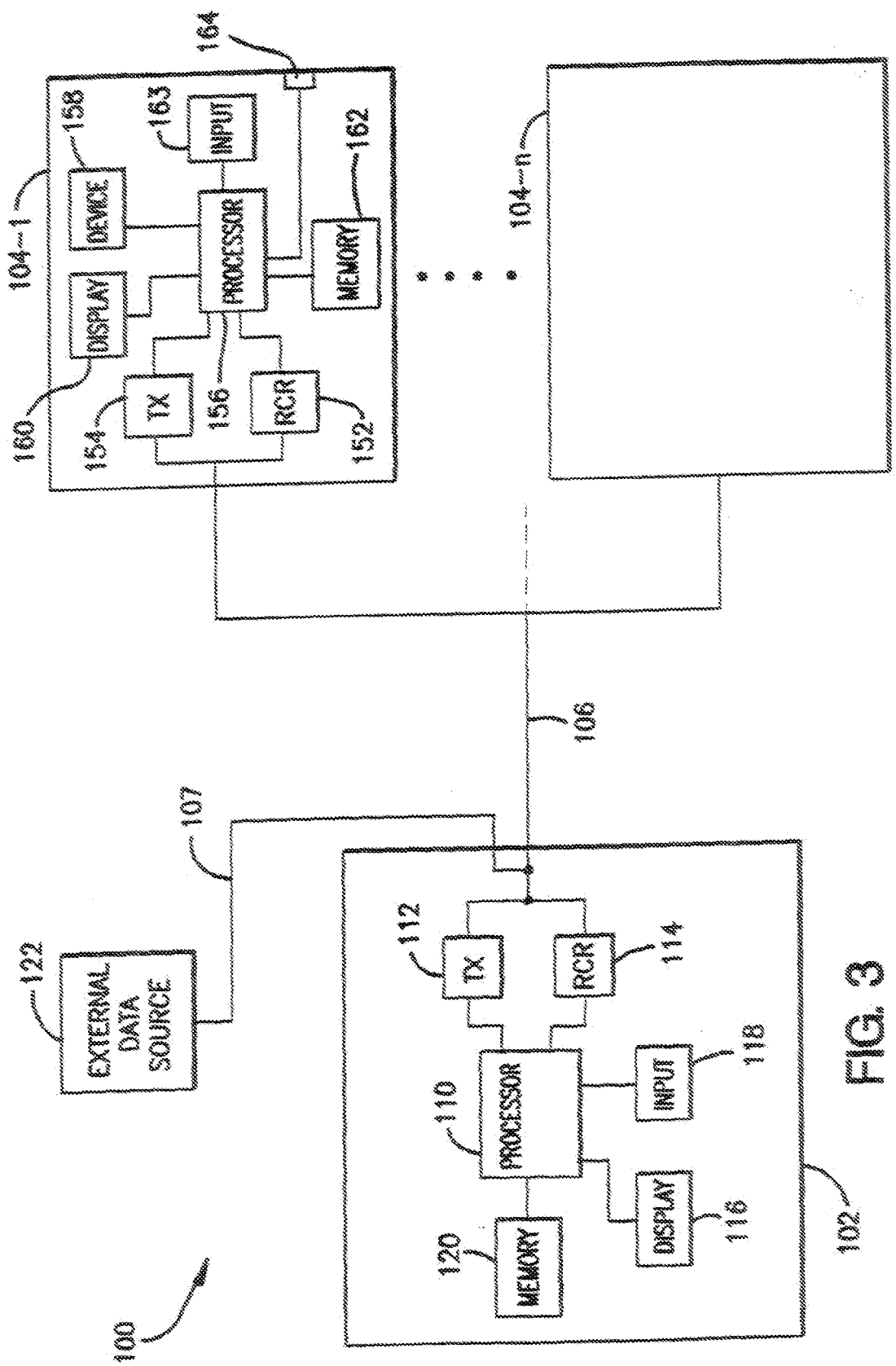
FIG. 3 is a block diagram of an exercise system in accordance with the present invention.

FIG. 3 is a block diagram of an exercise system 100 in accordance with the present invention. Exercise system 100 includes a central office 102 and one or more exercise apparatus 104-1 to 104-n which are remotely located with respect to central office 102. For example, exercise apparatus 104-1 to 104-n may be located in homes of exercisers and central office 102 may be located at a health club office, a personal trainer's office, or a physician's office. Alternatively, exercise apparatus 104-1 to 104-n may be located in a health club and central office 102 may be located in an office of the health club. Of course, the exercise apparatus and the central office may be otherwise located and the present invention is not limited in this respect. Data is communicated between central office 102 and exercise apparatus 104-1 to 104-n over a communication link 106. For example, data including software such as exercise programs, and text data such as news headlines, sports scores, stock market prices, weather reports, messages, advertisements, and the like may be transmitted from central office 102 to exercise apparatus 104-1 to 104-n over communication link 106. Also, data may be transmitted from the respective exercise apparatus to central office 102 over communication link 106. This data may, for example, be data indicating the number of times the respective exercise apparatus has been used or data indicating which exercise programs have been selected. The above examples of data which is communicated between central office 102 and exercise apparatus 104-1 to 104-n are provided for illustrative purposes only and other types of data may be communicated within the spirit and scope of the present invention.

Communication link 106 may, for example, be an infrared link, a radio frequency (RF) link, a coaxial cable, a telephone network, a satellite system, or an optical fiber. Although the embodiment of FIG. 3 shows only a single communication link, it will be apparent that a first communication link may be provided for data transmissions from central office 102 to exercise apparatus 104 and a second, different communication link may be provided for data transmissions from the exercise apparatus 104 to central office 102. In addition, data may be transmitted to the exercise apparatus from a first central office and data may be transmitted from the exercise apparatus to a second, different central office.

A processor 110 controls the overall operation of central office 102. A transmitter 112 transmits data over communication link 106 to the exercise apparatus 104-1 to 104-n. A receiver 114 receives data transmitted over communication link 106 from the exercise apparatus. A display device 116 such as a monitor displays information to a system operator and an input device 118 such as a keyboard permits the system operator to input information. Other output devices (not shown) such as a printer, speakers, etc, and other input devices (not shown) such as a mouse may also be provided. A memory 120 which may include both read only memory (ROM) and a non-volatile random access memory (NVRAM) stores an overall operating program for central office 102 as well as data to be described below with reference to FIG. 4. One or more external data sources 122 remotely located relative to central office 102 transmit data to central office 102 over a communication link 107. The data from the external data sources may then be forwarded to the exercise apparatus 104-1 to 104-n over communication link 106. For example, these external data sources may transmit exercise programs and/or text data such as news headlines, sports scores, stock market prices, weather reports, advertisements, etc. to central office 102. Processor 110 then supplies this data to memory 120 for storage and reads the data out at a later time for transmission by transmitter 112 to exercise apparatus 104-1 to 104-n. Central office 102 may also transmit data to the external data sources over communication link 107. Like communication link 106, communication link 107 may, for example, be an infrared link, an RF link, a coaxial cable, a telephone network, a satellite system, or an optical fiber.

Exercise apparatus 104-1 includes a receiver 152 for receiving data transmitted by central office 102 over communications link 106 and a transmitter 154 for transmitting data to central office 102 over communications link 106. A processor 156 controls the overall operation of the exercise apparatus. The exercise apparatus also includes an exercise device 158 which may be, for example, a stationary bicycle, stair climber, treadmill, rowing machine, or weight machine. A display 160 displays information to an exerciser. A memory 162 which may include a read-only memory and a non-volatile memory stores data for the operation of exercise apparatus 104-1. Data such as exercise programs and text items which is received by receiver 152 is supplied to memory 162 by processor 156. An input device 163 such as a keypad receives input from an exerciser. A port 164 may optionally be provided to connect the exercise apparatus to an external device such as a television or speakers. Exercise apparatus 104-2 to 104-n may be similarly configured.

Figure 4:
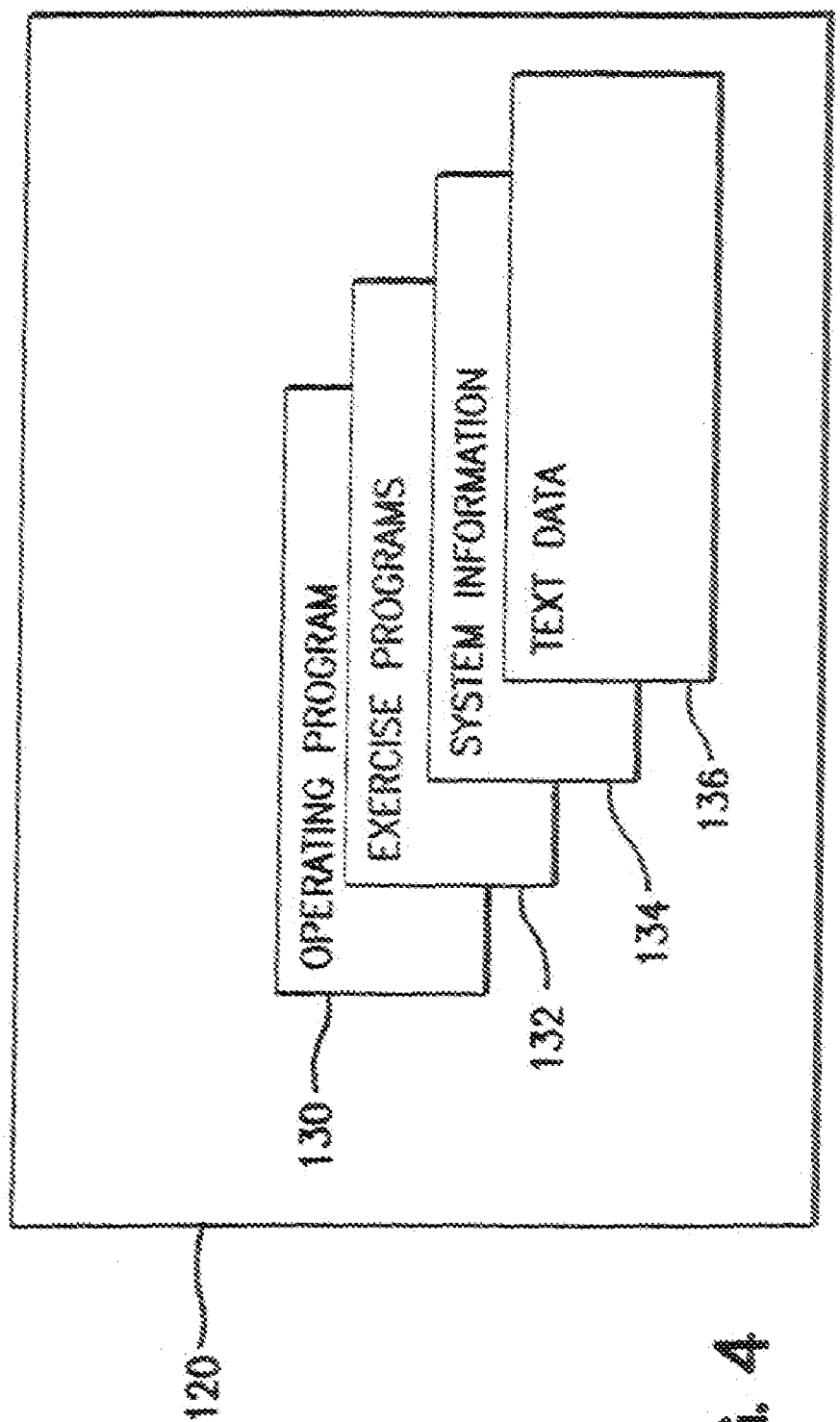
FIG. 4 is diagram illustrating the arrangement of memory 120 of FIG. 3.

With reference to FIG. 4, memory 120 of central office 102 includes a first memory portion 130 for storing an operating program for central office 102, a second memory portion 132 for storing exercise programs, a third memory portion 134 for storing system information, and a fourth memory portion 136 for storing text data. Memory 120 may be, for example, a magnetic disk drive, a battery backed-up non-volatile random access memory (NVRAM), or a PCMCIA EEPROM memory card. The information in the memory portions may be generated by the system operator or supplied from one or more of external data sources 122.

Second memory portion 132 stores at least one exercise program which is executable by one or more of the exercise apparatus 104. It will be appreciated that second memory portion 132 may store a variety of exercise programs suitable for use by different types and models of exercise apparatus. For example, one exercise program may be executable by a stationary bicycle of a first manufacturer to vary exercise level as a function of time while another exercise program may be executable by a stair climber of a second manufacturer to vary exercise level as a function of time. Accordingly each exercise program will preferably have associated therewith identification data for identifying the type and model of exercise apparatus for which the program is suitable. The exercise programs may be developed by the system operator or may be transmitted from one or more of the external data sources.

Third memory portion 134 stores system information. For example, each of the exercise apparatus 104-1 to 104-n may have associated therewith a unique apparatus identifier or address for identifying the exercise apparatus. The system information stored in third memory portion 134 may thus be organized in accordance with these apparatus identifiers. Third memory portion 134 may also store additional information regarding each exercise apparatus, for example, identification information identifying the type and model of exercise apparatus (stationary bicycle, stair climber, etc.) and program information listing the exercise programs currently stored in memory 162 of the exercise apparatus. Third memory portion 134 may also store the name, address, and telephone number of the owner of the exercise apparatus. Alternatively or in addition, third memory portion may store a name, address, and telephone number associated with the location of the exercise apparatus. If the exercise apparatus is linked to the central office over a telephone network, third memory portion 134 may also store the telephone number for establishing a telephone communication link between the central office and the exercise apparatus. Typically, the above-described data would be entered by the system operator, although the present invention is not limited in this respect.

Fourth memory portion 136 stores text data such as messages, news headlines, sports scores, stock market prices, weather reports, advertisements, and the like. This text data may be generated by the system operator and/or may be transmitted to central office 102 from one or more of external data sources 122.

The above-described functions of central office 102 may be implemented by a computer such as an IBM®.-compatible personal computer. The personal computer may include appropriate software for generating exercise programs which are executable by a microcomputer of the exercise apparatus 104-1 to 104-n and which, for example, specify the exercise level as a function of time. A program title, description, etc. may then be associated with each program as will be discussed below. The programs and associated information may then be stored on a hard-disk drive which serves as memory 120. The personal computer may be equipped with a modem and appropriate communications software for transmitting and receiving data including the above-described exercise programs and text data over a telephone line which serves as communication link 106. The modem and communications software may also be utilized to transmit and receive data from the external data sources 122 over communication link 107.

Figure 1:
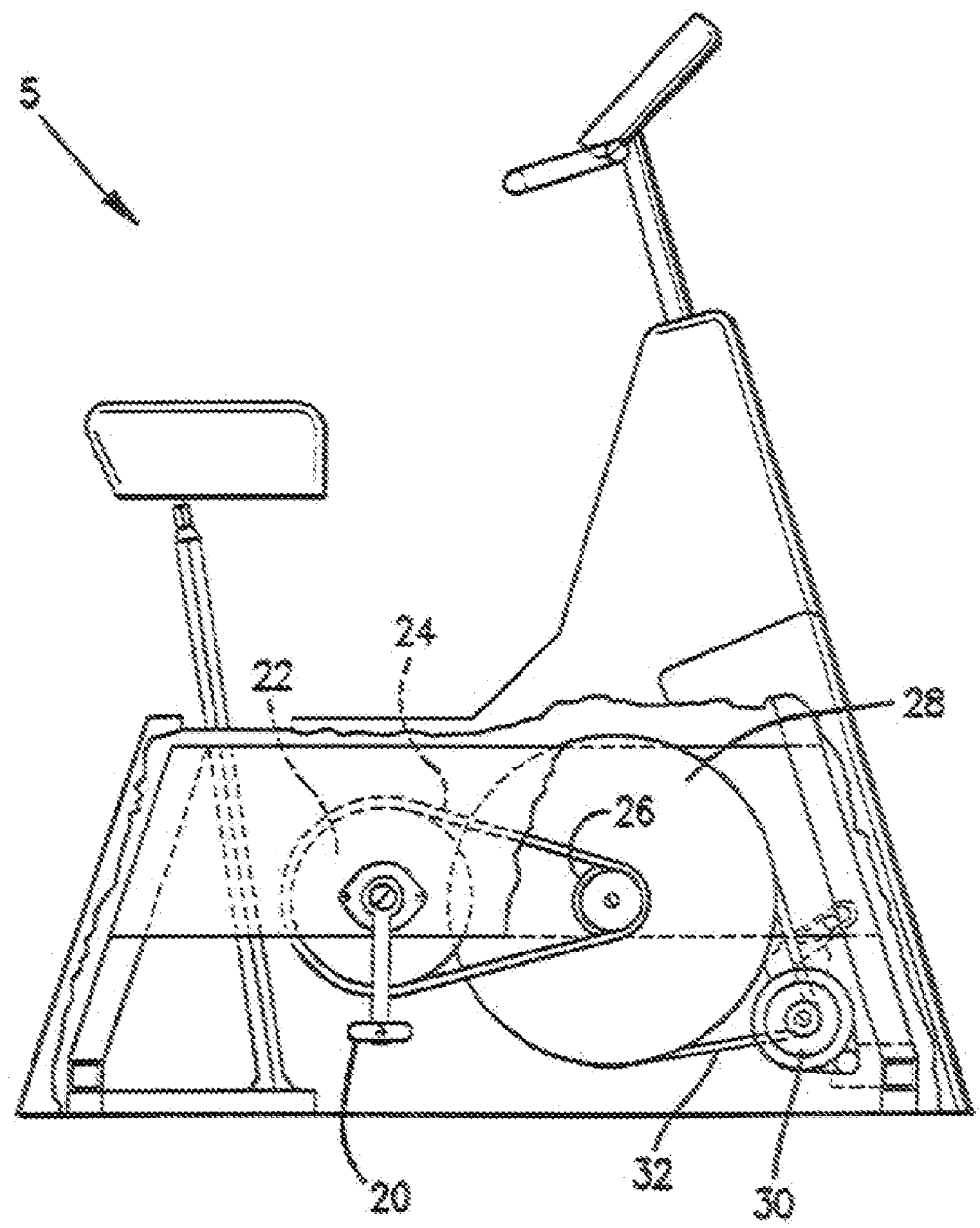
FIG. 1 is a side elevational view of a prior art stationary bicycle 5.
Figure 2:
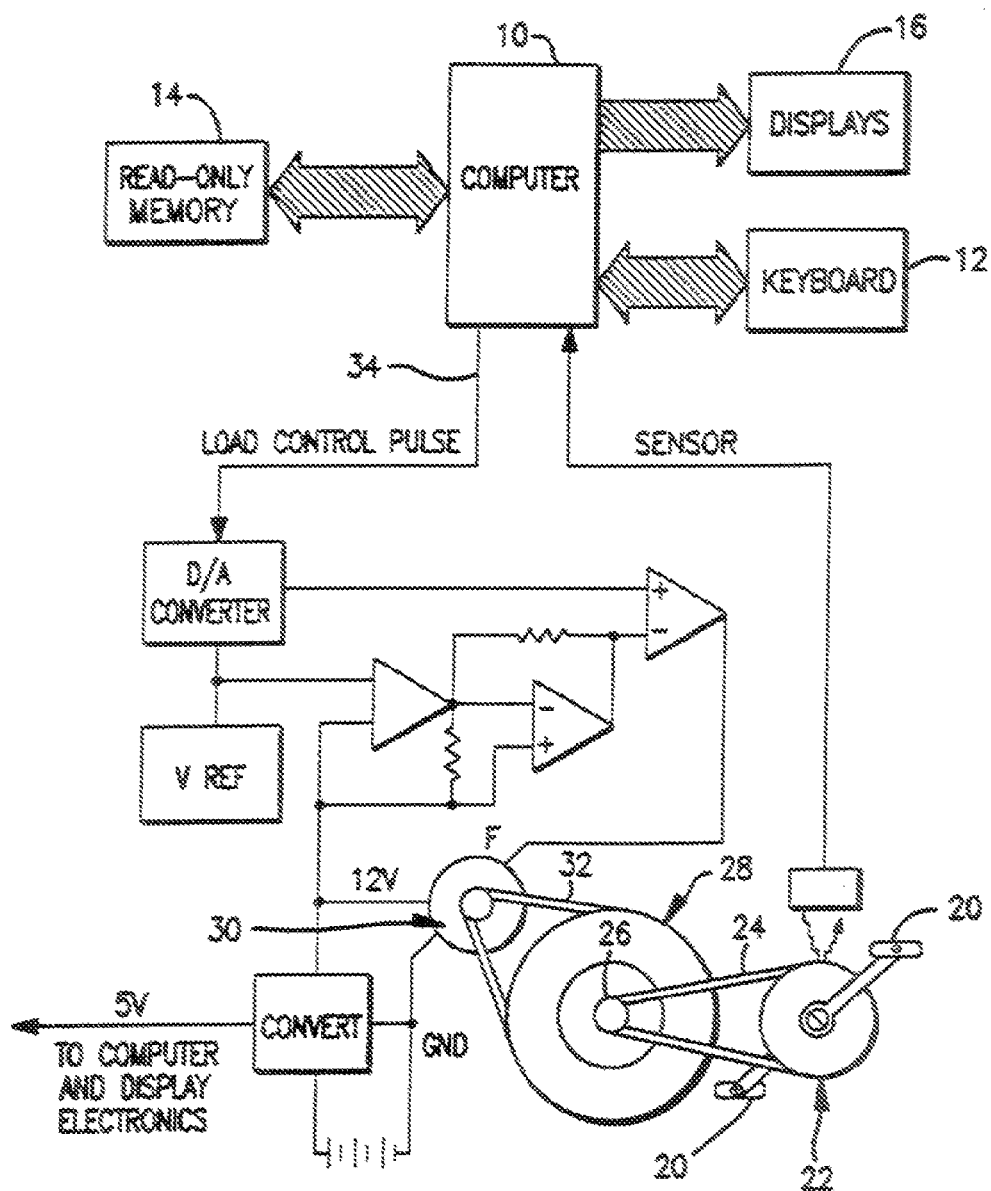
FIG. 2 is a schematic showing the electronic control system of stationary bicycle 5 of FIG. 1.
Figure 5:
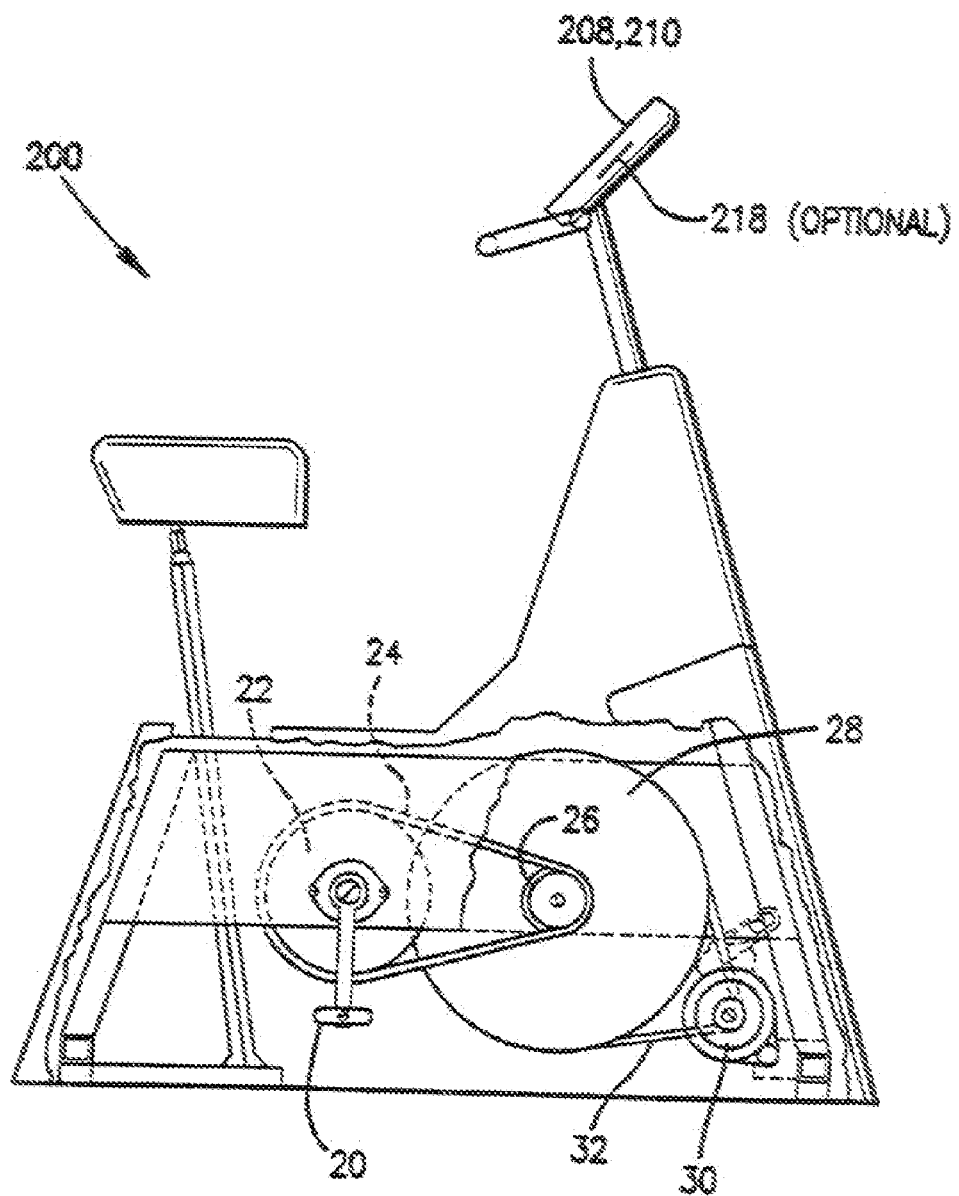
FIG. 5 is a side elevational view of a stationary bicycle 200 which may be utilized in the exercise system of the present invention.
Figure 6:
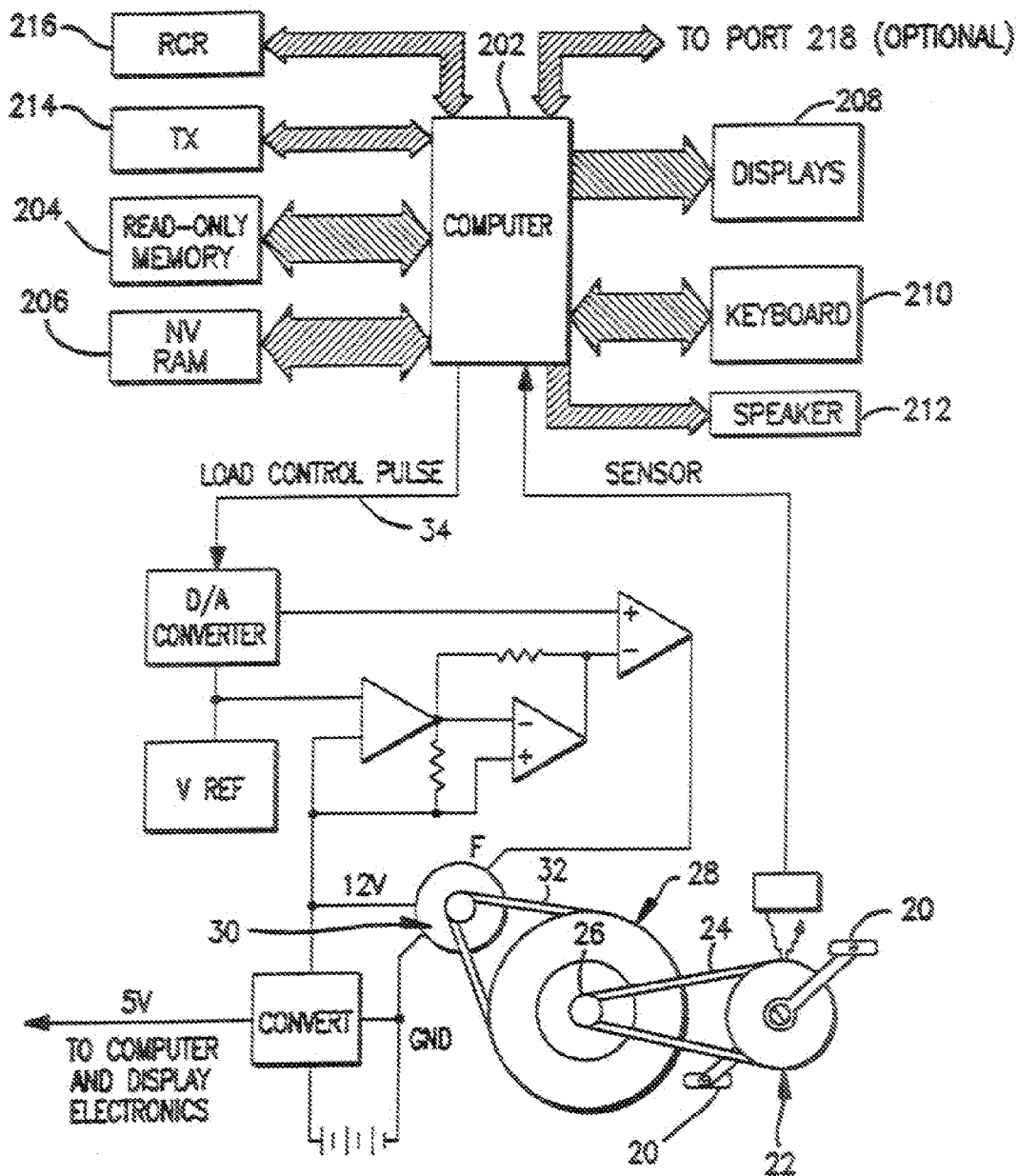
FIG. 6 is a schematic showing the electronic control system of stationary bicycle 200 of FIG. 5.

FIGS. 5 and 6 illustrate a stationary bicycle 200 which may be utilized as one of exercise apparatus 104 in accordance with the exercise system of the present invention. Elements of stationary bicycle 200 which are the same as those of stationary bicycle 5 shown in FIGS. 1 and 2 are designated with the same reference numbers and descriptions thereof are omitted. Although reference is made to a stationary bicycle, the teachings of the present invention are applicable to exercise systems which include any exercise apparatus having an exercise device controllable by a microcomputer in accordance with a program, including by way of example, but not by way of limitation, stationary bicycles, stair climbers, rowing machines, treadmills, and weight machines.

The control system of stationary bicycle 200 includes a microcomputer 202 for controlling the operation of stationary bicycle 200, a read-only memory (ROM) 204, a non-volatile random access memory (NVRAM) 206 (e.g., a battery backed-up random access memory), a display 208, a keypad 210, a speaker 212, a transmitter 214, and a receiver 216. An optional output port 218 may be provided to connect the exercise apparatus to one or more output devices 220 such a television or speakers.

ROM 204 stores an operating program of microcomputer 202 and may also contain various pre-stored exerciser-selectable programs for controlling stationary bicycle 200. Microcomputer 202 generates control signals supplied over line 34 for controlling the exercise level of stationary bicycle 200 in accordance with an exercise program selected either from ROM 204 or NVRAM 206. Display 208 includes, for example, light emitting diodes (LEDs) and/or liquid crystal displays (LCDs) and is responsive to signals from microcomputer 202 for displaying various information to the exerciser including, but not limited to, the exercise time, the exercise level, number of calories burned, and the like as is known in the art. Keypad 210 includes exerciser-operable keys for inputting various data as will be discussed below. Speaker 212 is responsive to microcomputer 202 for providing audible sounds to the exerciser to indicate, for example, the end of an exercise program or an incorrect selection or entry via keypad 210. Transmitter 214 transmits data to central office 102 over communication link 106 and receiver 216 receives data transmitted from central office 102 over communication link 106. If communication link 106 is a telephone network, for example, transmitter 214 and receiver 216 may be implemented by a modem which is coupled to a telephone line.

Figure 7:
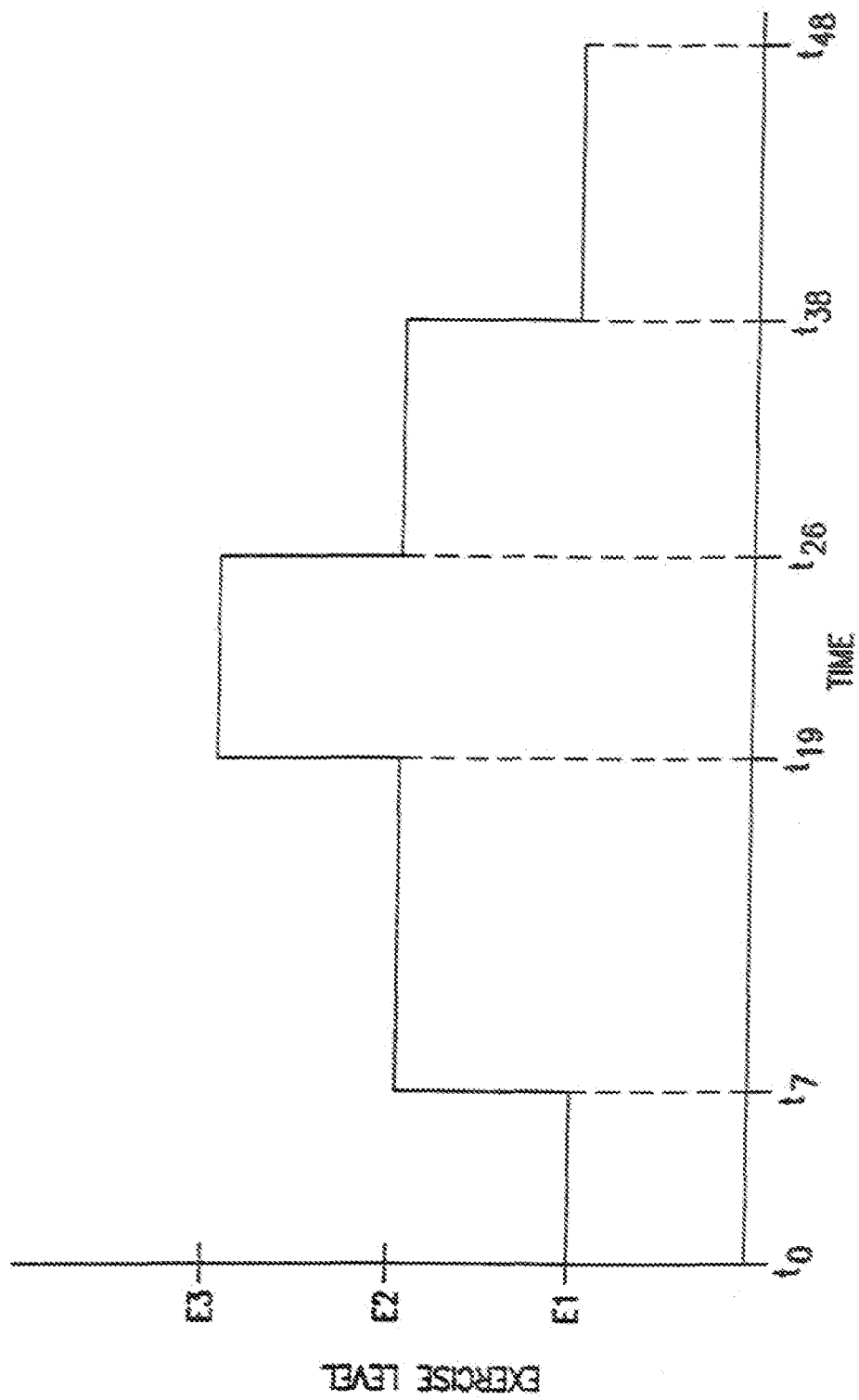
FIG. 7 is a graphical profile of exercise level versus time for an exercise program which may be utilized by microcomputer 202 of FIG. 6 to automatically control the exercise level of stationary bicycle 200.

An exercise program is executable by microcomputer 202 for automatically controlling stationary bicycle 200. FIG. 7 is a graphical profile of exercise level versus time for an illustrative, but non-limiting, exercise program which may be utilized by microcomputer 202 to automatically control the exercise level of stationary bicycle 200. As illustrated in the profile of FIG. 7, from exercise time $t_0$ until exercise time $t_7$, microcomputer 202 generates control signals for setting the exercise level of stationary bicycle 200 to exercise level E1; from exercise time $t_7$ until exercise time $t_{19}$, microcomputer 202 generates control signals for setting the exercise level of stationary bicycle 200 to exercise level E2; from exercise time $t_{19}$ until exercise time $t_{26}$, microcomputer 202 generates control signals for setting the exercise level of stationary bicycle 200 to exercise level E3; from exercise time $t_{26}$ until exercise time $t_{38}$, microcomputer 202 generates control signals for setting the exercise level of stationary bicycle 200 to exercise level E2; and from exercise time $t_{38}$ until exercise time $t_{48}$ (the end of the program), microcomputer 202 generates control signals for setting the exercise level of stationary bicycle 200 to exercise level E1. When a program having the profile of FIG. 7 is selected, an exerciser may select an exercise time over which microcomputer 202 will control stationary bicycle 200. The selection of an exercise time determines the time interval between the exercise times. For example, when an exercise program having the profile of FIG. 7 is selected, an exerciser may choose an exercise time of four, eight, twelve, sixteen, or twenty minutes. Depending on which total exercise time is selected, the time interval between the exercise times is five, ten, fifteen, twenty, or twenty-five seconds, respectively. An exerciser may also select a difficulty level which determines the difficulty of the exercise at the exercise levels of the program. The difficulty of exercise levels E1, E2, and E3 is generally less at low difficulty levels than at high difficulty levels. Thus, as the fitness level of an exerciser increases, higher difficulty levels may be utilized.

Of course, the exercise program of FIG. 7 is for illustrative purposes, and the present invention is not limited in this respect. Thus, an exercise program may also be of a type which provides interactivity via a visual display such as a television screen. For example, the execution of such a program may cause microcomputer 202 to monitor the activity level of the exerciser (e.g., how fast the exerciser is pedaling) via the SENSOR line shown in FIG. 6 and to output data to an output device 218 such as a television to thereby simulate a competition between the exerciser and a computer-generated opponent or opponents. For example, an exercise program for a stationary bicycle may generate a bicycle race between the exerciser and a computer-generated opponent. The "ability" of the opponent and the duration of the race may be set in accordance with the fitness level of the exerciser.

FIG. 8 is a table depicting an organization of exercise programs stored in NVRAM 206. Exercise program 1 is stored at memory location 1, defined for example, by a memory address. If desired, a program name and description may be associated with exercise program 1. Exercise programs 2, 3, . . . , n are stored at memory locations 2, 3, . . . , n as indicated. The operating program of microcomputer 202 stored in ROM 204 is configured to permit microcomputer 202 to access these exercise programs and to permit an exerciser to select an exercise program which is stored in memory 206. Of course, the exercise programs may be organized in various ways in memory 206 and the invention is not limited in this respect. In addition, as noted above, one or more exercise programs may be stored in a portion of ROM 204, if desired, using a memory organization similar to that illustrated in FIG. 8. If exercise programs are stored in a portion of ROM 204, the operating program is configured to permit an exerciser to select an exercise program which is stored in either ROM 204 or memory 206.

Figure 9:
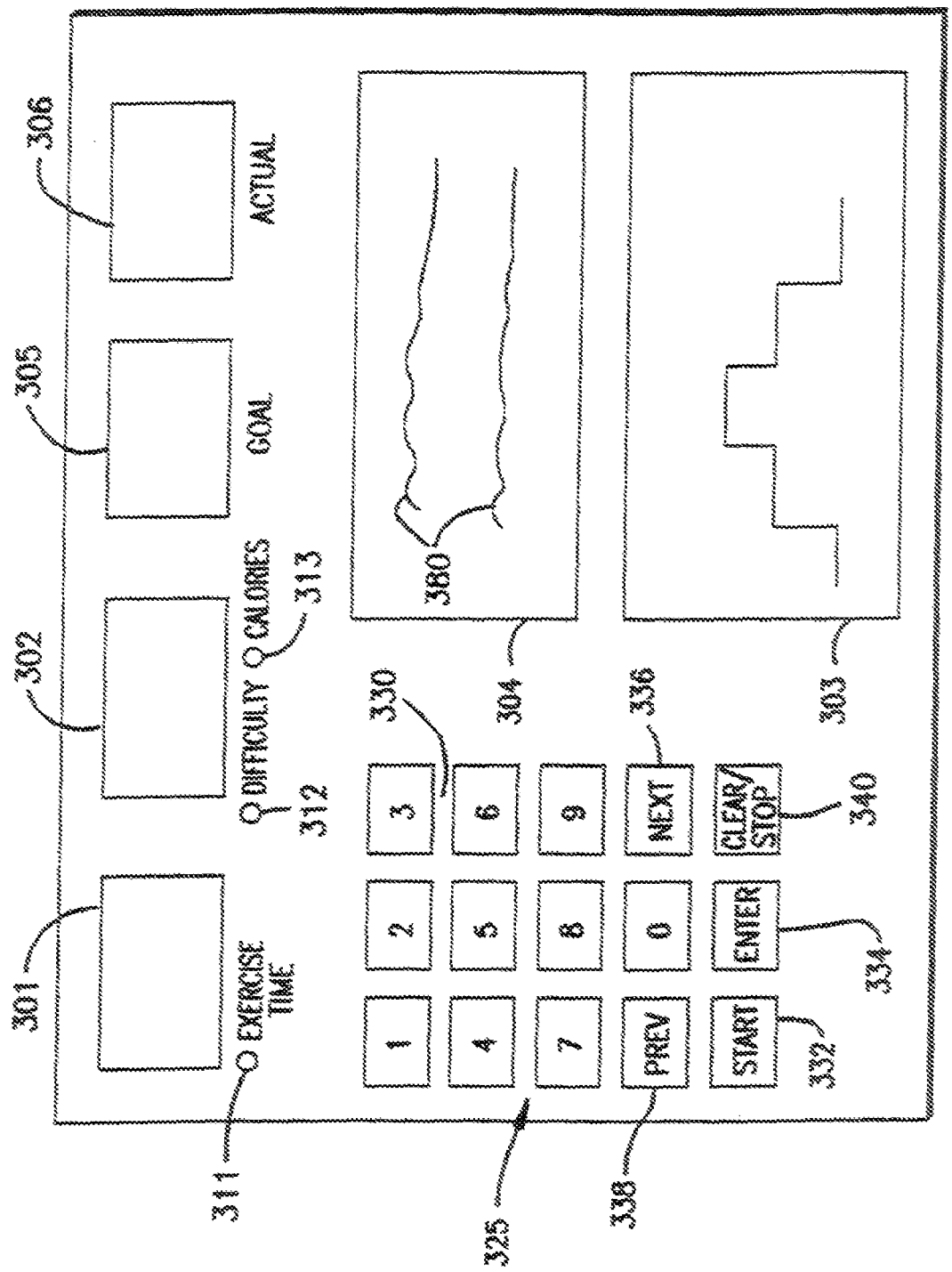
FIG. 9 illustrates display 208 and keypad 210 shown in FIG. 5.

FIG. 9 illustrates display 208 and keypad 210 arranged on a display and keypad panel. Display 208 includes various display portions 301-306. During program selection, display portion 301, exercise time indicator 311, and difficulty level indicator 312 prompt an exerciser to enter an exercise time and difficulty level for an exercise program. During exercise, display portion 301 displays an elapsed exercise time while display portion 302 alternately displays the current difficulty level of the exercise program and the number of calories burned. Exercise time indicator 311, difficulty level indicator 312, a calories burned indicator 313 are LEDs, for example, which are appropriately illuminated to indicate which quantity should be entered by the exerciser during program selection and/or which quantity is being displayed during the exercise time. Exercise level display portion 303 displays a graphical profile of exercise level versus time for the exercise program such as is shown, for example, in FIG. 7. Display portion 304 is a line display including one or more lines 380 which may display graphical and text information such as program names and descriptions, operating instructions, and text data items to an exerciser. Display portion 305 provides a display relating to how fast an exerciser should be pedaling stationary bicycle 200 at a current exercise level and display portion 306 provides a display of how fast an exerciser is actually pedaling. Displays of other information may also be provided, if desired. It will be appreciated that the displays of stationary bicycles and other exercise apparatus may be varied in accordance with the information which it is desired to display and the present invention is not limited in this respect. Keypad 325 includes a numeric keyboard portion 330 having numeric keys. 0-9; a START key 332; an ENTER key 334; a NEXT key 336; a PREV (previous) key 338; and a CLEAR/STOP key 340.

The transmitting of exercise programs and text data from central office 102 to exercise apparatus 104-1 to 104-$n$ will now be described. The system operator may select one or more exercise programs from second memory portion 132 and/or text data from fourth memory portion 136 for transmission to one of exercise apparatus or to a group of exercise apparatus. For example, the system operator may transmit exercise programs and text data to a group of exercise apparatus which are of the same type and model. Processor 110 supplies the selected exercise programs and/or text data from memory 120 to transmitter 112 for transmission to the exercise apparatus. For example, if communication link 106 is a telephone network and transmitter 112 is a modem, processor 110 utilizes appropriate communication software to transmit the data the next time a telephone link is established between central office 102 and the exercise apparatus. This may occur either when the central office dials an appropriate telephone number to connect the central office to the exercise apparatus or when the exercise apparatus dials a telephone number of the central office to connect the exercise apparatus to the central office. When a connection is established, the data is downloaded from the central office to the exercise apparatus. At the time of this connection, data may also be uploaded from the exercise apparatus to the central office. The telephone connections may be established automatically at specified times as controlled by processor 110 or microcomputer 202 or may be initiated by the system operator. The exerciser may prompt an exercise apparatus to establish a telephone connection with the central office by pressing a button (not shown) provided on keypad 210. Of course, the telephone link described above is for illustrative purposes only and other techniques may be utilized for the purpose of establishing a communication link between the central office and the exercise apparatus. For example, data may be broadcast to the exercise apparatus via an in-band or out-of-band data channel of a conventional cable television system. Data may be addressed to particular exercise apparatus in the same manner that data is addressed to particular subscriber terminals. Specifically, the exercise apparatus may be connected to an exercise apparatus data port of a subscriber terminal in a cable television system. A processor or application specific integrated circuit (ASIC) of the subscriber terminal supplies the exercise program and text data to the exercise apparatus data port and this data is then output to the receiver of the exercise apparatus. The processor of the exercise apparatus supplies the data received by the receiver to memory 162 of the exercise apparatus. For example, with respect to the stationary bicycle of FIGS. 5 and 5 and 6, exercise programs received by receiver 216 may be supplied to a first memory portion of NVRAM 206 and text data received by receiver 216 may be supplied to a second memory portion of NVRAM 206.

To select an exercise program, an exerciser actuates START key 332. Microcomputer 202 prompts the exerciser to select an exercise program. Exercise programs are selectable from among the programs stored in NVRAM 206 and, if provided, from any programs stored in ROM 204. The exerciser may be prompted to select an exercise program by, for example, displaying the program name and description on line display portion 304 and additionally or alternatively displaying a corresponding graphical profile of the exercise level versus time on display portion 303. The exerciser is able to step forward and backward through the available exercise programs using NEXT key 336 and PREV key 338. For example, using the NEXT key 336 and PREV key 338, an exerciser may cause microcomputer 202 to step forward and backward through the programs in ROM 204 and/or NVRAM 206. To select an exercise program whose program name, program description, and/or profile is displayed, the exerciser actuates ENTER key 334. If appropriate for the selected exercise program, the exerciser is prompted to enter an exercise time and difficulty level. When these values have been appropriately entered, microcomputer 202 controls stationary bicycle 200 in accordance with the exercise program, exercise time, and difficulty level. Microcomputer 202 may also update a third memory portion of NVRAM 206 to indicate a use of the exercise apparatus and to indicate which exercise program was selected. During execution of the program, microcomputer 202 controls display 208 to display data such as the elapsed exercise time to the exerciser, current difficulty level, RPM-GOAL, RPM-ACTUAL, and the like. Display portion 303 may be appropriately illuminated to indicate an exerciser's progress through the exercise profile. At the end of the exercise program, microcomputer 202 drives speaker 212 to output an audible sound indicating the end of the program. Program execution may be stopped prior to the end of the program by pressing CLEAR/STOP key 340.

An almost limitless number of exercise programs may be developed in which the exercise level of the exercise device is varied over time or in which a simulated competition is generated. By providing an arrangement in which exercise programs may be downloaded into the exercise apparatus, the on-board memory of the exercise apparatus may be provided with a wide variety of new exercise programs from which an exerciser may select.

In addition to downloading exercise programs, central office 102 may also download text data including news headlines, sports scores, stock market prices, weather reports, advertisements, and the like. In addition, a system operator may generate a text message which may be sent to particular exercise apparatus. The text message may, for example, describe new exercise programs or exercise equipment which is or will be available. This text data may be displayed to the exerciser on line display 304 while the exerciser is exercising in order to provide a mental activity for the exerciser. Microcomputer 202 may cause line display 304 to display each text data item for a predetermined period of time or up and down arrow keys (not shown) may be provided to permit the exerciser to step through the text data items. These text items may be periodically downloaded to exercise apparatus 104, for example, every 24 hours, when one or more exercise programs are downloaded, or when data is uploaded to the central office. Of course, the text items are not limited to news headlines, sports scores, stock market prices, weather reports, and advertisements.

As noted above, although the above description is based on a stationary bicycle, the present invention is generally applicable to any exercise apparatus controllable in accordance with a program. Such apparatus are manufactured, for example, by Life Fitness, Nautilus, Schwinn, and the like. Thus, for example, for a treadmill, control signals may control the speed of the tread and/or the inclination of the tread to the horizontal. For a stair climber, the control signals may control the resistance of the pedals. For a weight machine, the control signals may control the resistance.

Each of the above-referenced patent documents is hereby incorporated by reference into the instant specification.

While there has been shown and described the preferred embodiments of the invention, it will be evident to those skilled in the art that various modifications may be made thereto without departing from the spirit and scope of the invention which is set forth in the appended claims.

I claim:

1. A system for distributing exercise programs to different locations comprising:
    a processor; and
    communication circuitry under the control of the processor and configured to communicate a first exercise program to a first exercise apparatus of a first exercise type at a first location and a second exercise program to a second exercise apparatus of a second exercise type at a second location remote from the first location, the first exercise program for use in control of the first exercise apparatus and the second exercise program for use in control of the second exercise apparatus.

2. The system according to claim 1, wherein the communication circuitry is further configured to communicate mental activity data to the first and second exercise apparatuses.

3. The system according to claim 2, wherein the mental activity data comprises display data.

4. A system for distributing exercise program information to different locations comprising:
    a processor; and
    communication circuitry under the control of the processor and configured to communicate first exercise program information to a first exercise apparatus of a first exercise type at a first location and second exercise program information to a second exercise apparatus of a second exercise type at a second location remote from the first location, the first exercise program information for use in control of a movable element of the first exercise apparatus and the second exercise program information for use in control of a movable element of the second exercise apparatus.

5. The system according to claim 4, wherein the first exercise apparatus comprises a treadmill and the second exercise apparatus comprises a stationary bicycle.

6. The system according to claim 4, wherein the first and second exercise apparatuses are located in different homes.

7. The system according to claim 4, wherein the movable element of the first exercise apparatus comprises pedals.

8. The system according to claim 4, wherein the communication circuitry under the control of the processor is further configured to communicate messages to the first and second exercise apparatuses.

9. The system according to claim 4, further comprising:
a memory for storing information for the first and second exercise apparatuses including respective identifiers associated with the first and second exercise apparatuses.

10. The system according to claim 9, wherein the information further comprises apparatus owner information.

11. The system according to claim 4, further comprising:
a memory for storing information for the first and second exercise apparatuses including respective addresses associated with the first and second exercise apparatuses.

12. The system according to claim 11, wherein the information further comprises apparatus owner information.

13. The system according to claim 4, wherein the communication circuitry is further configured to communicate mental activity data to the first and second exercise apparatuses.

14. The system according to claim 4, wherein the first and second exercise program information comprises respective programs for use in controlling the movable elements of the first and second exercise apparatuses as a function of time.

15. A system in which exercise-related information is communicated to and from different locations comprising:
a computer system configured to provide exercise-related information; and
first and second exercise apparatuses each of a different exercise type and each at a different home,
wherein the computer system is configured to communicate first exercise-related program information to the first exercise apparatus and second exercise-related information to the second exercise apparatus, the first exercise-related information including information for use in control of a movable element of the first exercise apparatus and the second exercise-related information including information for use in control of a movable element of the second exercise apparatus, and
wherein each of the first and second exercise apparatuses is configured to communicate additional exercise-related information to the computer system.

16. The system according to claim 15, wherein the first exercise apparatus comprises a treadmill and the second exercise apparatus comprises a stationary bicycle.

17. The system according to claim 15, wherein the first and second exercise apparatuses provide different types of exercise.

18. The system according to claim 15, wherein the computer system is further configured to communicate mental activity data to the first and second exercise apparatuses and the first and second exercise apparatuses are configured to output the mental activity data.

19. The system according to claim 15, wherein the movable element of the first exercise apparatus comprises pedals.

20. The system according to claim 15, wherein the computer system is further configured to communicate messages to the first and second exercise apparatuses.

21. The system according to claim 15, wherein the computer system comprises memory for storing information for the first and second exercise apparatuses including respective identifiers associated with the first and second exercise apparatuses.

22. The system according to claim 15, wherein the computer system comprises memory for storing information for the first and second exercise apparatuses including respective addresses associated with the first and second exercise apparatuses.

23. The system according to claim 15, wherein each of the first and second exercise apparatuses comprises a panel including a liquid crystal display, the panel further comprising a pressable input device for initiating communication with the computer system.

* * * * *